United States Patent [19]

Glage

[11] 4,059,100

[45] Nov. 22, 1977

[54] MASSAGING APPARATUS

[75] Inventor: Ulrich Glage, Hamburg, Germany

[73] Assignee: Gisela Glage nee Möller, Hamburg, Germany

[21] Appl. No.: 697,475

[22] Filed: June 18, 1976

[30] Foreign Application Priority Data

June 20, 1975 Germany .............................. 2528093

[51] Int. Cl.² .......................... A61H 1/00; A61H 19/00
[52] U.S. Cl. ............................................ 128/36; 128/79
[58] Field of Search ..................................... 128/32–41, 128/24.2, 79, 294, 44, 62

[56] References Cited

FOREIGN PATENT DOCUMENTS 835,637   4/1952   Germany .............................. 128/79
825,137   12/1951  Germany .............................. 128/79

Primary Examiner—Lawrence W. Trapp
Attorney, Agent, or Firm—Fleit & Jacobson

[57] ABSTRACT

An apparatus for massaging elongated parts of the human body, especially for applying massage to stimulate and improve the ability for erection, comprises an elongated sheath which is excitable to controlled vibrations of two superimposed frequencies.

10 Claims, 1 Drawing Figure

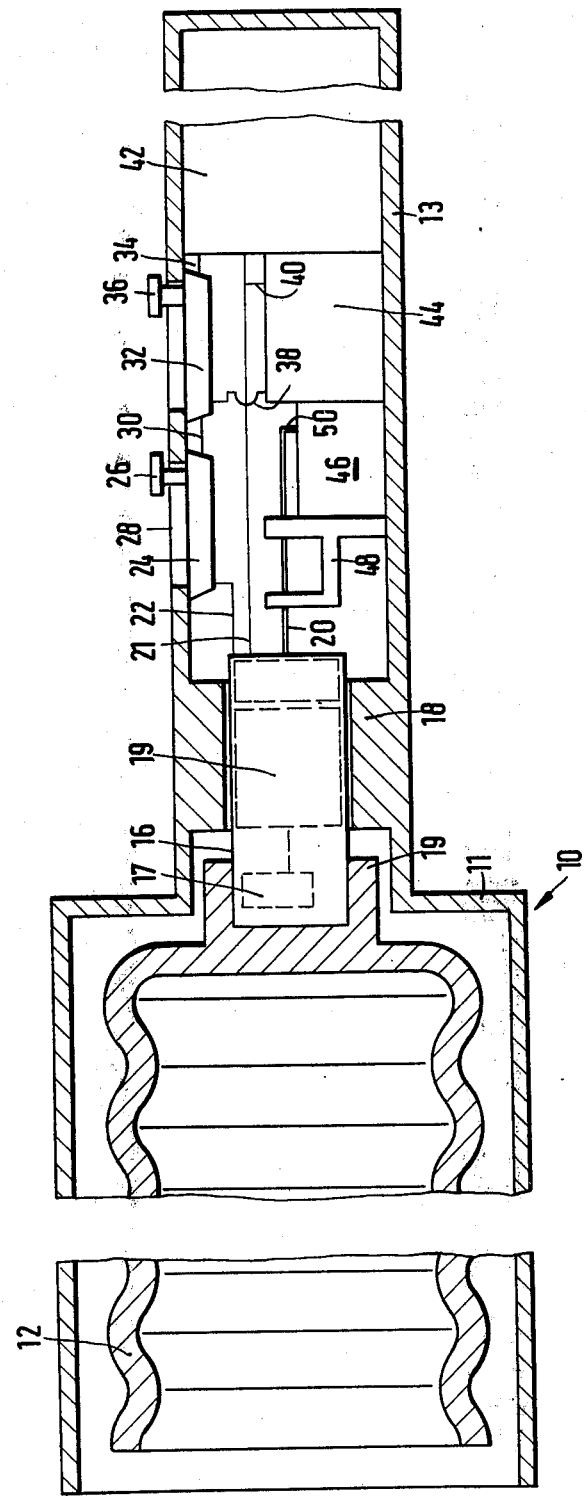

MASSAGING APPARATUS

The invention relates to a device or apparatus for massaging elongated parts of the human body, and especially for applying massage to stimulate and enhance the ability for erection.

German Pat. No. 825,137 describes an open ended enveloping cylinder which fits over the organ for treatment, and which can then be evacuated. The vacuum pressure which is thus generated inside the enveloping cylinder is intended to stimulate engorgement of the corpus cavernosum of the organ. German Pat. No. 835,637 describes a sleeve consisting of elastic material and a pumping device in the form of a simple rubber ball which is connected to a self-contained cavity embracing the sleeve, and thus adapted to constrict the cross section of the sleeve.

The main object of the present invention is the provision of an appliance which is capable of providing a kind of massage that is as natural as possible. A further object of the invention is the provision of an easy-to-handle massage apparatus. Another object of the invention is an easily controllable device for massaging. It is also an object of the invention to provide a power driven massage apparatus.

For achieving these and further objects, the invention provides an apparatus for massage comprising an elongated hollow cylindrical sheath having one closed end and so designed that the outside of the sheath is connected to a vibrating device containing means for the simultaneous generation of two different mechanical vibrations. Preferably the vibrating device is located at the closed end of the sheath. The invention further proposes that the vibrating device should comprise two coupled vibrators connected to the sheath. Preferably a first vibrator generates vibrations normal to the longitudinal axis of the hollow cylinder. A second vibrator generates vibrations parallel to the longitudinal axis of the sheath. It is further proposed that the vibrations generated by the second vibrator should have a lower frequency than those generated by the first vibrator.

The vibrators the invention proposes to use may be on the one hand an eccentric weight driven by a miniature electric motor and on the other hand a miniature motor provided with gearing for converting its rotary motion into an axially reciprocatory motion, this reciprocation being transmitted to the axially movably mounted first vibrator.

As a power source for driving an appliance according to the invention it is proposed to use a number of dry batteries, so-called monocells, which may be contained in the same housing as the vibrators. In the interests of handling convenience the current source may also be accommodated in a separate casing.

The proposed appliance is characterised by a particularly apposite effect and by an extremely simple form of construction which despite the presence of the coupling for the transmission of the vibrations nevertheless readily permits the hollow cylindrical sheath to be replaced.

Further objects, advantages and features of the invention will be understood from the claims and from the following particular description and the accompanying drawing which illustrates a preferred embodiment of the invention.

The only drawing is a simplified axial section of an apparatus according to the invention.

Referring to the drawing the proposed apparatus comprises a housing 10 consisting preferably of "perspex" or a like synthetic plastics. Housing 10 contains substantially two portions. That portion which in the drawing is on the left is a hollow cylinder which is open at its left hand end, whereas at the other end it has an inner radial flange 11 integrally connected to a housing portion 13 which in the illustrated embodiment is likewise elongated and cylindrical.

The left hand larger diameter portion of housing 10 coaxially contains an elongated hollow cylindrical sheath 12. Sheath 12 is likewise open-ended at the left whereas the other end is formed with a cylindrical mount 14 which firmly fits over the end of a first vibrator 16. Preferably the sheath is made of latex by the immersion technique. However, a synthetic plastics material could also be used provided its surface and elastic properties were the same or at least similar to those of the latex. Sheath 12 is formed with regularly spaced corrugations which improve the effect of the massage. Mount 14 allows for easy replacement of sheath 12.

Mount 14 of sheath 12 is fitted directly to a first vibrator 16 which is supported in a slide bearing 18 of preferably integral construction with portion 13 of the housing. Substantially this vibrator 16 consists of an electric motor 19 and an eccentric weight 17 mounted on the shaft of electric motor 19. Electric motor 19 is connected by leads 21, 22, switch means 24, 26, and conductors 30 and 34 to a source of power 42 which is only diagrammatically shown. Switch means 24, 26 may be combined with a sliding variable resistor which permits the speed of the motor 19 and hence the frequency of the vibrations generated by eccentric or out-of-balance weight 17 to be controlled. These vibrations are rotary vibrations in a plane normal to the longitudinal axis of the sheath 12. The tight fit of mount 14 on vibrator 16 provides a sufficiently tight coupling for distributing the vibrations around the sheath 12.

First vibrator 16 which is supported by slide bearing 18 in the radial direction is attached to a rod 20 mounted in a two-armed bearing bracket 48. Rod 20 is connected by a radial arm 50 to a transmission 46 which converts the rotary motion of the drive shaft of an electric motor 44 into an axially reciprocatory motion of rod 20. The electric motor 44 is connected on the one hand by a branch 40 and lead 21, and, on the other hand, by a lead 38, a switch means 32, 36 and a conductor 34 to power source 42. Switch means 32, 36 likewise incorporates a variable sliding resistor. For this purpose the control button 36 of the switch projects through an axial slot 28 in portion 13 of the housing, as does control button 26 of the first above-mentioned switch.

First vibrator 16 and electric motor 19 including the eccentric weight 17 may be an assembly of the kind otherwise used in the toy-making industry. Similarly, the second vibrator comprising Electric motor 44 and motion transformer 46 may also be an assembly used in the toy-making industry.

Power source 42 is preferably composed of a plurality of monocells. In order to reduce the overall dimensions of the apparatus proper the power source may be accommodated in a special case connected to the main part of the device by electric leads. Since the first vibrator 16 is axially shiftable by the distance representing the amplitude of the vibration generated by the second vibrator 44, 46 the leads 21, 22 which are indicated in the drawing by straight lines are coiled wires which allow for a considerable extension in length.

When the apparatus is switched on by operation of the button controls 26 and 36 the first vibrator generates radial vibrations which are applied through mount 14 to sheath 12. At the same time the rod 20 which is attached to the first vibrator 16 axially reciprocates the sheath 12 at the frequency of the second vibrator 44, 46. The control means permit these combined vibrations to be so matched that the frequency of first vibrator vibrator 16 exceeds that of second vibrator 44, 46.

I claim:

1. A massaging apparatus comprising an elongated hollow sheath having a first end and a second end opposite to each other, said first end being open, means for simultaneously generating two different mechanical vibrations, coupling means for connecting said vibration generating means with said sheath.

2. A massaging apparatus according to claim 1 wherein closing means and said coupling means are provided at said second end.

3. A massaging apparatus according to claim 1 wherein common housing means enclose said vibration generating means, said coupling means and at least a part of said sheath adjacent to said coupling means, said first open end being accessible by an opening of said housing.

4. A massaging apparatus according to claim 3 wherein said elongated hollow sheath defines a longitudinal axis and said vibration generating means comprises a first and a second vibrator, said first vibrator having a power driven eccentric weight for generating vibrations normal to said longitudinal axis, and said coupling means comprises sleeve means having an axis coinciding with said longitudinal axis, said sleeve means being connected to said second end of said sheath and interengaging with a part of said first vibrator.

5. A massaging apparatus according to claim 1 wherein said sheath consists of latex.

6. A massaging apparatus according to claim 1 wherein said sheath is substantially cylindrical and provided with a plurality of corrugations at its inner wall.

7. A massaging apparatus according to claim 1 wherein said vibration generating means comprises two coupled mechanical vibrators, said vibrators being driven by electrical motor means.

8. A massaging apparatus according to claim 3 wherein said elongated hollow sheath defines a longitudinal axis and said vibration generating means comprises power driven first and second vibrators, said first vibrator having an eccentric weight for the generation of vibrations normal to said longitudinal axis and being mounted in a slide bearing of said housing for reciprocating motion in parallel to said longitudinal axis, said second vibrator comprising output means reciprocatingly moving in parallel to said longitudinal axis, said output means being mechanically connected with said first vibrator.

9. A massaging apparatus according to claim 8 wherein electric motor means and gear means are provided said gear means transforming a rotary motion of said electric motor means into a reciprocating motion.

10. A massaging apparatus according to claim 9 wherein said electric motor means comprises a first motor for said first vibrator, a second motor for said second vibrator and control means for independently switching and controlling said first and said second motor.

* * * * *